United States Patent [19]

Schnettler et al.

[11] Patent Number: 4,803,278

[45] Date of Patent: Feb. 7, 1989

[54] PREPARATION OF 1,3-DIHYDRO-4-PYRIDOYL-2H-IMIDAZOL-2-ONES

[75] Inventors: Richard A. Schnettler; Chi-Hsin R. King, both of Cincinnati, Ohio

[73] Assignee: Merrell Dow Pharmaceuticals, Inc., Cincinnati, Ohio

[21] Appl. No.: 916,131

[22] Filed: Oct. 7, 1986

Related U.S. Application Data

[63] Continuation-in-part of Ser. No. 820,280, Jan. 17, 1986, abandoned, which is a continuation of Ser. No. 754,191, Jul. 10, 1985, abandoned, which is a continuation of Ser. No. 635,852, Jul. 30, 1984, abandoned.

[51] Int. Cl.$^4$ .......................................... C07D 401/02
[52] U.S. Cl. .................................. 546/278; 546/315; 546/328; 546/334; 546/338
[58] Field of Search ......................................... 546/278

[56] References Cited

U.S. PATENT DOCUMENTS 4,405,628  9/1983  Dage et al. ........................ 546/278

OTHER PUBLICATIONS

House, *Modern Synthetic Reactions*, 2nd Edit., 1972, pp. 9–10, 17, 150–3, and 209–11.
March, *Advanced Organic Chemistry*, 2nd Edit., 1977, pp. 1082–1084.

*Primary Examiner*—Mary C. Lee
*Assistant Examiner*—Kurt G. Briscoe
*Attorney, Agent, or Firm*—J. Michael Dixon

[57] ABSTRACT 1,3-Dihydro-4-pyridoyl-2H-imidazol-2-ones are prepared in a three step process by
(a) reducing 1-pyridyl-1,3-deketo-2-oximinoalkanes to produce 1-pyridyl-1-hydroxy-2-amine-3-ketoalkanes;
(b) reacting the thus produced hydroxyaminoketone with cyanate ion to produce a 1,3-dihydro-4-hydroxy(pyridyl)methyl-2H-imidazol-2-one; and
(c) oxidizing the thus produced hydroxymethyl compound to yield the desired product.

5 Claims, No Drawings

PREPARATION OF 1,3-DIHYDRO-4-PYRIDOYL-2H-IMIDAZOL-2-ONES

CROSS REFERENCE TO RELATED APPLICATIONS

This is a continuation-in-part of application Ser. No. 820,280, filed Jan. 17, 1986, now abandoned, which is a continuation of application Ser. No. 754,191, filed July 10, 1985, now abandoned, which is a continuation of application Ser. No. 635,852, filed July 30, 1984, now abandoned.

BACKGROUND OF THE INVENTION

The present invention is directed to a process for producing 1,3-dihydro-4-pyridoyl-2H-imidazol-2-ones of Formula I

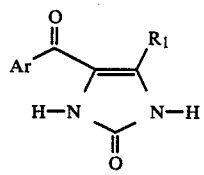

wherein $R_1$ is a hydrogen or a 1 to 4 carbon atom alkyl group and Ar is a 2-, 3- or 4-pyridyl group as well as the pharmaceutically acceptable salts thereof. These compounds and in particular 4-ethyl-1,3-dihydro-5-(4-pyridoyl)-2H-imidazol-2-one possess potent cardiotonic utility and are useful therapeutic agents in the treatment of cardiac failure.

These compounds have been prepared in the prior art by several methods. In one method an imidazol-2-one is reacted with a pyridoyl chloride or bromide or pyridine carboxylic acid or carboxylic acid anydride in the presence of a Lewis acid catalyst, typically aluminum chloride. This process suffers from several serious drawbacks upon scale-up including extreme difficulty in mixing the solid aluminum complexes and resultant poor yields primarily due to difficulty in separating product from the solid mass of the reaction pot.

In another prior art reaction illustrated in Scheme I, a diketo-oxime of structure II is reduced to form an aminodiketone of structure III which upon reaction with a cyanate salt yields the structure I compounds.

SCHEME I

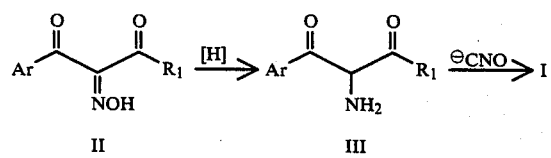

Several difficulties are encountered when this process is employed. In particular, because the keto function adjacent to the pyridine ring in the structure II compounds is activated towards hydrogenation, this keto group is reduced along with the oxime group to yield to hydroxyaminoketones of formula IV.

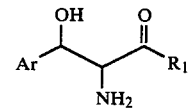

This side reaction necessitates removal of the structure IV compounds from the hydrogenated reaction mixture and results in lowered overall yields of the desired structure I compounds.

Applicants have discovered that improved yields of the desired product of structure I can be obtained following the reaction path of Scheme III.

SCHEME III

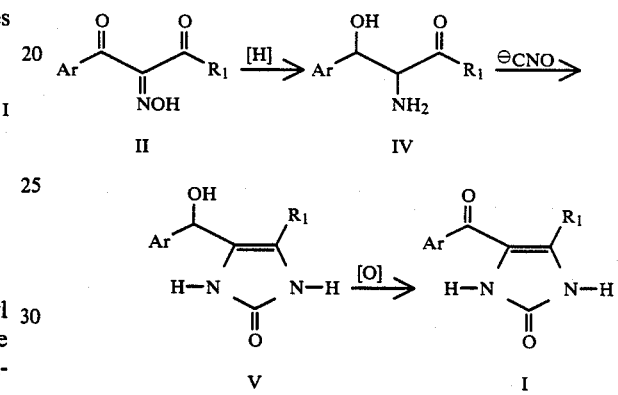

This improved reaction scheme eliminates the need to remove any of the hydroxyaminoketone of formula IV which forms by undesired side reaction in the scheme II process. Moreover, the reaction of the hydroxyaminoketone of formula IV with cyanate ion in scheme III proceeds with substantially greater yields of cyclized product than does the corresponding reaction of the diketoamino compound of structure III with cyanate ion in the scheme II process. Applicants have found, surprisingly, that the overall conversion of structure II compound to the desired pyridoylimidazol-2-one of structure I proceeds with substantially greater overall yields when the process of scheme III is utilized rather than that of scheme II. This occurs even though the scheme III process requires an additional step which has no counterpart in the closely related prior art process of scheme II, that is, scheme III requires the oxidation of the structure V alcohol to produce the desired pyridoylimidazol-2-one.

SUMMARY OF THE INVENTION

In accordance with this invention, pyridoylimidazol-2-ones of formula I are prepared by a three step process from the diketo-oximes of formula II as illustrated in scheme III. More particularly, the process of the present invention comprises reducing a diketo-oxime of structure II employing either hydrogen and a metallic catalyst or a dissolving metal to produce the hydroxyaminoketones of formula IV which after cyclization with a cyanate salt are oxidized with a N-haloimide to produce the desired pyridoylimidazol-2-one of formula I.

DETAILED DESCRIPTION OF THE INVENTION

The applicants have discovered a process whereby a pyridoylimidazol-2-one of structure I can be prepared by sequentially reducing, cyclizing and oxidizing a diketo-oxime of structure II. The process of this invention is readily adapted to large scale batch production of structure I compounds in yields greater than other known methods.

As used herein, the term "a 1 to 4 carbon atom alkyl group" means a methyl, ethyl, propyl, isopropyl, n-butyl, or isobutyl group.

The starting materials, the diketo oximes of structure II, are readily prepared by any suitable procedure known in the art such as nitrosation of the corresponding diketone of formula VI wherein $R_1$ is a hydrogen or a 1 to 4 carbon atom alkyl group and Ar is a 2-, 3- or 4-pyridyl group.

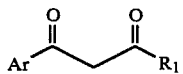

VI

Suitable nitrosation reactions are reviewed by O. Tousler in "Organic Reactions", Volume VII, pages 327–377.

Although the reduction of the diketo-oximes of structure II to yield the hydroxyaminoketones of structure IV can be accomplished in any manner known to those skilled in the art using any suitable reducing agents, applicants have now discovered that reductions involving either hydrogen gas with a metallic catalyst or a dissolving metal provides yields of product far greater than expected. Applicants have employed either (a) hydrogen gas in the presence of a 10% Palladium on Charcoal catalyst using acetic acid solvent followed by a dilute acid workup or (b) zinc metal and formic acid or acetic acid. Because the hydroxyamino-ketones are unstable when isolated as the free bases, it is advisable to isolate these structure IV compounds as acid addition salts. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxygenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophilic organic solvents and which in comparison to their free base forms, are substantially more stable.

The reductions of this invention involving dissolving metals can be performed using suitable active metals such as zinc, magnesium, tin or iron and organic acids such as methaneslfonic, acetic or formic acid or a mineral acid such as sulfuric or hydrochloric acid. The diketo-oxime to be reduced is dissolved in a suitable, nonreactive solvent such as ethanol, isopropanol, n-butyl alcohol, isoamyl alcohol, or water, and the acid is added. This solution is then slowly added to a slurry of the metal reductant, preferably zinc dust, in formic acid and the mixture stirred until the reaction is complete, typically from 5 minutes to 10 hours, preferably from about 1 to 2 hours. The reaction time will vary depending on the reactants, the solvent and the temperature which can be from 0° to 150° C. preferably from 25° to 80° C. The product can be isolated from the reaction mixture either as the free base or preferably as an acid addition salt in any manner commonly employed by those skilled in the art. For example, if 10% methanol in isopropanol is added to the concentrated residue, the hydroxyaminoketone will precipitate from the solution and can then be separated by filtration.

Alternatively, the reductions of this invention involving hydrogen gas and a metallic catalyst can be performed using any suitable catalyst, for instance, palladium, platinum, ruthenium, rhodium, platinum dioxide, each either in powder form or adsorbed on a carrier such as charcoal or Raney nickel. The diketo-oxime to be reduced is dissolved in a suitable solvent, a small amount of catalyst is added, preferably less than 10 percent by weight of the amount of compound to be reduced, and the reaction allowed to proceed until 3 equivalents of hydrogen gas are taken up. The amount of time required will depend upon the compound to be reduced, the pressure of hydrogen gas used which can be from 1 to 10 atmospheres, preferably 1 atmosphere, the solvent and the temperature which can be from 0° to 50° C., preferably about 25° C. Suitable solvents include any non-reactive solvent including ethyl acetate, ethanol, water, or preferably acetic acid. When the reaction is complete, hydrochloric acid or any other suitable mineral acid is added to the reaction mixture which is then filtered to remove the solid catalyst. The hydroxyaminoketone or an acid addition salt thereof can then be recovered by any suitable method readily known to those skilled in the art including simple solvent removal.

The cyclization of the hydroxyaminoketones of structure IV with cyanate ion to produce the hydroxymethylimidazol-2-ones of structure V can be carried out by the ordinary artisan in any suitable manner. Typically, the hydroxyaminoketone and from 1 to 5 molar equivalents, preferably about 2 molar equivalent of a cyanate salt are allowed to react for from about 5 minutes to about 24 hours depending on the reactants, the solvent and the temperature which can be from −78° to about 100° C. preferably from about 0° to 50° C. Suitable solvents for this reaction are any nonreactive solvent such as water or a water miscible solvent, for example, an organic acid such as acetic acid; an alcohol such as methanol or ethanol; or an ether such as diethyl ether, tetrahydrofuran or p-dioxan. Preferably, any nonaqueous solvent is mixed with water. The preferred solvent is water. Any source of cyanate ion may be utilized in the cyclization reaction. Applicants have utilized potassium cyanate but any simple alkali or alkaline earth salt such as lithium, sodium or calcium cyanate as well as a transition group metal cyanate would be useful.

The product of this reaction of an acid addition salt thereof can be isolated by any art-known procedure such as by conversion to the corresponding sodium or potassium salt and reprecipitation with carbon dioxide or a mineral acid such as dilute hydrochloride acid.

The final step of the scheme III process wherein a hydroxyimidazol-2-one of formula V is oxidized to yield the desired pyridoylimidazol-2-one of formula I can be carried out in any convenient manner by procedures readily known to those skilled in the art. However, applicants have discovered that oxidation with an N-haloimide such as 1,3-dibromo-5,5-dimethylhydantoin, 1,3-dichloro-5,5-dimethylhydantoin, N-chloroacetamide, N-bromosuccinimide or preferably N-chlorosuccinimide produce yields of product greatly in excess of expectations. These oxidations are performed by dissolving the compound to be oxidized in a suitable solvent to which 1 to 5 molar equivalents, preferably about 1 molar equivalent, of the N-haloimide is added. The reaction temperature can be from about $-78°$ C. to about $80°$ C., preferably from about $0°$ C. to $60°$ C. and will require from ½ hour to about 48 hours, preferably from 10 to 18 hours, to be complete depending on the reactants, the solvent and other reaction conditions. Suitable solvents include any nonreactive solvents such as dimethylacetamide, methanol, dimethylformamide or preferably dimethylformamide-methanol cosolvent. The resulting product of Structure I can be isolated in any appropriate manner generally known to those skilled in the art such as by precipitation and subsequent recrystalization.

The following specific Examples more clearly illustrate the process of making and using this invention and set forth the best mode contemplated by the inventors for carrying out their invention. However, these illustrations are not to be construed as limiting the scope of the invention claimed.

EXAMPLE 1

Preparation of
1-(4-Pyridyl)-1-hydroxy-2-amino-3-ketopentane

In 1000 ml acetic acid was dissolved 23.0 g (0.11 mol) of 1-(4-pyridyl)-1,3-diketo-2-oximinopentane. The solution is charged with 1.0 g of 10% palladium on carbon and hydrogenated until three equivalents of hydrogen were taken up. The mixture was acidified with 18.5 ml of 12N hydrochloric acid, filtered and the solvent evaporaed to give the title compound as the dihydrochloric acid salt; m.p. 225° C.

Following the procedure of Example 1 above but substituting:
1-(2-pyridyl)-1,3-diketo-2-oximinopentane;
1-(4-pyridyl)-1,3-diketo-2-oximinobutane;
1-(3-pyridyl)-1,3-diketo-2-oximinopropane;
1-(4-pyridyl)-1,3-diketo-4-methyl-2-oximinopentane; or
1-(2-pyridyl)-1,3-diketo-2-oximinoheptane; for the:
1-(4-pyridyl)-1,3-diketo-2-oximinopentane
results in:
1-(2-pyridyl)-1-hydroxy-2-amino-3-ketopentane;
1-(4-pyridyl)-1-hydroxy-2-amino-3-ketobutane;
1-(3-pyridyl)-1-hydroxy-2-amino-3-ketopropane;
1-(4-pyridyl)-1-hydroxy-2-amino-4-methyl-3-ketopentane; or
1-(2-pyridyl)-1-hydroxy-2-amino-3-ketoheptane; respectively.

EXAMPLE 2

Preparation of
1-(4-Pyridyl)-1-hydroxy-2-amino-3-ketopentane

In 20 ml acetic acid is dissolved 1.0 g of 1-(4-pyridyl)-1,3-diketo-2-oximinopentane with heat (50° C.). The solution is acidified with dry hydrogen chloride and 1.0 g of zinc dust is slowly added. The mixture is stirred for one hour and cooled. Dry ether is added to the mixture and the title compound precipitates from the solution as a crude solid. This may be used in subsequent steps without purification.

Following the above procedure but employing:
1-(3-pyridyl)-1,3-diketo-4-methyl-2-oximinohexane;
1-(4-pyridyl)-1,3-diketo-2-oximinoheptane;
1-(3-pyridyl)-1,3-diketo-4-methyl-2-oximinopentane;
in place of:
1-(4-pyridyl)-1,3-diketo-2-oximinopentane;
results in:
1-(3-pyridyl)-1-hydroxy-2-amino-4-methyl-3-ketohexane;
1-(4-pyridyl)-1-hydroxy-2-amino-3-ketoheptane; or
1-(3-pyridyl)-1-hydroxy-2-amino-4-methyl-3-ketopentane;
respectively.

EXAMPLE 3

Preparation of
1-(4-Pyridyl)-1-hydroxyl-2-amino-3-ketopentane

In 37.8 kg of 88% formic acid was dissolved 7.5 kg (91% pure, 36.37 mole) of 1-(4-pyridyl)-1,3-diketo-2-oximinopentane and 7.0 kg of methanesulfonic acid. The resulting solution was slowly added to a slurry of 8.3 kg of zinc powder in 35.7 kg of formic acid. The reaction temperature was kept at about 60° C. by proper cooling and slow addition. The mixture was allowed to stir at 55° C. for 2 hours and then cooled to 20° C. The solid zinc formate was filtered off. To the formic acid filtrate was added 3.6 kg of methanesulfonic acid. The formic acid was removed at the reduced pressure (40 mm Hg) and 70° C. To the residue was added a solution of 5.9 kg of methanol and 53.3 kg of isopropanol and stirred at 20° C. for 4 hours. Solid material was collected by centrifugation, washed with 12.5 kg of 10% methanol in isopropanol giving 11.0 kg, 87% yield, of the title compound as dimethanesulfonate salt after drying.

EXAMPLE 4

Preparation of
4-Ethyl-1,3-dihydro-5-[hydroxy(4-pyridyl)methyl]-2H-imidazol-2-one In 100 ml water is dissolved 29.0 g (0.11 mol) of 1-(4-pyridyl)-1-hydroxy-2-amino-3-ketopentane dihydrochloride and 17.9 g (0.22 mol) of potassium cyanate. The solution is warmed to 50° C. for 10 minutes and then allowed to stand at room temperature for 10 hours, cooled and the solid collected to give the title compound; m.p. 234°-36°.

Following the procedure described above in Example 4 but using:
1-(2-pyridyl)-1-hydroxy-2-amino-3-ketopentane;
1-(4-pyridyl)-1-hydroxy-2-amino-3-ketobutane;
1-(3-pyridyl)-1-hydroxy-2-amino-3-ketopropane;
1-(4-pyridyl)-1-hydroxy-2-amino-4-methyl-3-ketopentane;
1-(2-pyridyl)-1-hydroxy-2-amino-3-ketoheptane;
1-(3-pyridyl)-1-hydroxy-2-amino-4-methyl-3-ketohexane;
1-(4-pyridyl)-1-hydroxy-2-amino-3-ketoheptane; or
1-(3-pyridyl)-1-hydroxy-2-amino-4-methyl-3-ketopentane;
instead of:
1-(4-pyridyl)-1-hydroxy-2-amino-3-ketopentane results in:
1,3-dihydro-4-ethyl-5-[hydroxy(2-pyridyl)methyl]-2H-imidazol-2-one;
1,3-dihydro-4-[hydroxy(4-pyridyl)methyl]-5-methyl-2H-imidazol-2-one;
1,3-dihydro-4-[hydroxy(3-pyridyl)methyl]-2H-imidazol-2-one;
1,3-dihydro-4-[hydroxy(4-pyridyl)methyl]-5-(1-methyl)ethyl-2H-imidazol-2-one;
4-butyl-1,3-dihydro-5-[hydroxy(2-pyridyl)methyl]-2H-imidazol-2-one;
1,3-dihydro-4-[hydroxy(3-pyridyl)methyl]-5-(1-methyl)propyl-2H-imidazol-2-one;
4-butyl-1,3-dihydro-5-[hydroxy(4-pyridyl)methyl]-2H-imidazol-2-one; or
1,3-dihydro-4-[hydroxy-(3-pyridyl)methyl]-5-(1-methyl)ethyl-2H-imidazol-2-one;
respectively.

EXAMPLE 5

1,3-Dihydro-4-ethyl-5-(4-pyridoyl)-2H-imidazol-2-one

To a slurry of 4.6 kg of 4-ethyl-1,3-dihydro-5-[hdroxy(4-pyridy)methyl]-2H-imidazol-2-one in 2.9 kg of methanol and 14.0 kg of dimethylformamide was added a solution of 2.8 kg of N-chlorosuccinimide in 17.0 kg of dimethylformamide over a 2-hour period at 0° C. The resulting mixture was stirred at 0° C. for 5 hours and then warmed up to 60° C. for 3 hours. To the reaction mixture was added a solution of 1.7 kg of sodium acetate and 0.39 kg of sodium metabisulfite in 5.5 kg of water and stirred at 25° C. for 4 hours. The resulting mixture was concentrated by vacuum distillation (at 80° C. and 24 mm Hg) to remove 21 kg of solvents. To the concentrated solution was added 17.5 kg of water with stirring and cooled at −4° C. for 12 hours. Solid material was collected by centrifuge to give 3.3 kg (72% yield, 99% purity) of the title compound after drying.

What is claimed is:

1. A process for the preparation of pyridoylimidazol-2-one of the formula

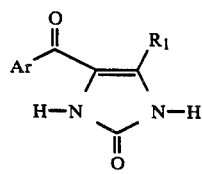

wherein Ar is a 2-, 3- or 4-pyridyl group and $R_1$ is hydrogen or a 1 to 4 carbon atom alkyl group which comprises oxidizing an hydroxymethylimidazol-2-one of the formula

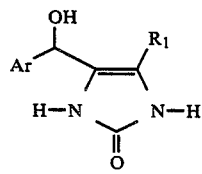

wherein Ar and $R_1$ are as defined above with a N-haloimide and recovering the product.

2. A process of claim 1 wherein the hydroxymethylimidazol-2-one is oxidized with N-chlorosuccinimide.

3. A process of claim 1 wherein Ar is a 4-pyridyl group and $R_1$ is a hydrogen or a 1 to 4 carbon atom alkyl group.

4. A process for the preparation of a pyridoylimidazol-2-one of the formula

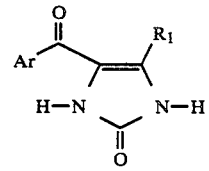

wherein Ar is a 2-, 3- or 4-pyridyl group and $R_1$ is a hydrogen or a 1 to 4 carbon atom alkyl group which comprises:

(a) reducing a diketo-oxime of the general formula

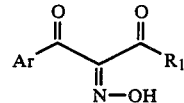

wherein Ar and $R_1$ are as defined above with hydrogen gas and a metallic catalyst or a dissolving metal to produce an hydroxyiminoketone of the formula

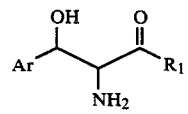

wherein Ar and $R_1$ are as defined above;

(b) cyclizing the thus produced hydroxyiminoketone by reaction with a cyanate ion to produce an hydroxymethylimidazol-2-one of the general formula

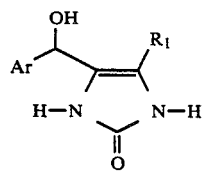

wherein Ar and $R_1$ are as defined above; and (c) oxidizing the thus produced hydroxymethylimidazol-2-one with an N-haloimide to produce the desired pyridoylimidazol-2-one and isolating the product.

5. A process of claim 4 wherein the diketo-oxime is reduced by a mixture consisting of zinc metal, formic acid and methanesulfonic acid and wherein the hydroxymethylimidazol-2-one is oxidized with N-chlorosuccinimide.

* * * * *